（12） United States Patent
DeLine et al.

(10) Patent No.: US 8,747,106 B2
(45) Date of Patent: Jun. 10, 2014

(54) POWER PRODUCTION USING GRAIN FRACTIONATION PRODUCTS

(75) Inventors: Kenneth E. DeLine, Avon, CO (US); Daniel L. Claycamp, West Frankfort, IL (US); Daniel Fetherston, Cape Girardeau, MO (US)

(73) Assignee: MOR Technology, LLC, Metropolis, IL (US)

( * ) Notice: Subject to any disclaimer, the term of this patent is extended or adjusted under 35 U.S.C. 154(b) by 1721 days.

(21) Appl. No.: 11/792,149

(22) PCT Filed: Nov. 22, 2006

(86) PCT No.: PCT/US2006/045193
§ 371 (c)(1),
(2), (4) Date: Jun. 1, 2007

(87) PCT Pub. No.: WO2008/020865
PCT Pub. Date: Feb. 21, 2008

(65) Prior Publication Data
US 2009/0239185 A1    Sep. 24, 2009

Related U.S. Application Data

(60) Provisional application No. 60/838,642, filed on Aug. 18, 2006, provisional application No. 60/858,107, filed on Nov. 10, 2006.

(51) Int. Cl.
*F23C 99/00* (2006.01)
*C12P 7/06* (2006.01)
(52) U.S. Cl.
USPC .......................................... 431/253; 435/161

(58) Field of Classification Search
None
See application file for complete search history.

(56) References Cited

U.S. PATENT DOCUMENTS

| 2,662,842 | A | * | 12/1953 | Christensen ................... 435/99 |
| 4,018,755 | A | | 4/1977 | Wang |
| 4,059,604 | A | | 11/1977 | Kresse |
| 4,083,836 | A | | 4/1978 | Anjou et al. |
| 4,325,882 | A | | 4/1982 | Reiners |
| 4,341,713 | A | | 7/1982 | Stolp et al. |
| 4,422,903 | A | * | 12/1983 | Messick et al. ................. 203/19 |
| 4,495,207 | A | | 1/1985 | Christianson et al. |

(Continued)

FOREIGN PATENT DOCUMENTS

| CN | 1242416 | 1/2000 |
| CN | 1522596 | 8/2004 |

(Continued)

OTHER PUBLICATIONS

Best et al., "The economic feasibility of operating an advanced ethanol production facility in Georgia", University of Georgia Center for Agribusiness and Economic Development, Aug. 2005.*

(Continued)

*Primary Examiner* — Patricia A Leith
*Assistant Examiner* — Erin M Bowers
(74) *Attorney, Agent, or Firm* — Craig R. Miles; CR Miles, P.C.

(57) ABSTRACT

An energy independent dry corn fractionation ethanol production system which utilizes at least one product of a dry corn fractionation process as fuel to generate power for the production of ethanol. Specifically, power production devices and methods of generating power from dry corn fractionation products for the production of ethanol.

19 Claims, 9 Drawing Sheets

(56) References Cited

U.S. PATENT DOCUMENTS

| | | | |
|---|---|---|---|
| 4,515,726 A | 5/1985 | Sullivan | |
| 4,576,820 A | 3/1986 | Hussmann | |
| 4,859,371 A | 8/1989 | Diosady et al. | |
| 4,898,673 A | 2/1990 | Rice et al. | |
| 4,994,272 A | 2/1991 | Hussmann | |
| 5,138,075 A | 8/1992 | Ohgaki et al. | |
| 5,250,313 A | 10/1993 | Giguere | |
| 5,252,729 A | 10/1993 | De Crosta et al. | |
| 5,295,629 A | 3/1994 | Satake et al. | |
| 5,498,384 A | 3/1996 | Volk et al. | |
| 5,680,812 A | 10/1997 | Linsgeseder | |
| 5,685,218 A | 11/1997 | Kemper | |
| 5,759,549 A | 6/1998 | Hiltunen et al. | |
| 5,826,500 A | 10/1998 | Kemper | |
| 5,997,877 A | 12/1999 | Chang | |
| 6,201,142 B1 * | 3/2001 | Maza | 554/16 |
| 6,254,914 B1 | 7/2001 | Singh et al. | |
| 6,326,035 B1 | 12/2001 | Nakatani et al. | |
| 6,368,649 B1 | 4/2002 | van Bommel | |
| 6,495,175 B2 | 12/2002 | Rao et al. | |
| 6,504,085 B1 | 1/2003 | Howard | |
| 6,570,030 B2 | 5/2003 | Goto et al. | |
| 6,664,405 B2 | 12/2003 | Lee | |
| 6,814,998 B1 | 11/2004 | Ozawa et al. | |
| 6,899,910 B2 | 5/2005 | Johnston et al. | |
| 6,936,110 B2 * | 8/2005 | Van Thorre | 127/68 |
| 6,936,294 B2 | 8/2005 | Matthews et al. | |
| 6,953,165 B1 | 10/2005 | Griebat et al. | |
| 7,037,548 B2 | 5/2006 | Ozawa et al. | |
| 7,074,449 B1 | 7/2006 | Holley et al. | |
| 7,087,720 B2 | 8/2006 | Murray et al. | |
| 2003/0019736 A1 * | 1/2003 | Garman | 203/23 |
| 2003/0068415 A1 * | 4/2003 | Taylor et al. | 426/316 |
| 2004/0234649 A1 | 11/2004 | Lewis et al. | |
| 2005/0016525 A1 * | 1/2005 | Thorre | 127/68 |
| 2005/0233030 A1 | 10/2005 | Lewis et al. | |
| 2005/0239181 A1 | 10/2005 | Lewis et al. | |
| 2006/0035354 A1 | 2/2006 | Galli et al. | |
| 2007/0037267 A1 | 2/2007 | Lewis et al. | |

FOREIGN PATENT DOCUMENTS

| | | |
|---|---|---|
| GB | 366516 | 1/1932 |
| GB | 707385 | 4/1954 |
| GB | 1058076 | 2/1967 |
| GB | 1398459 | 6/1975 |
| JP | 6136384 | 5/1994 |
| JP | 6299187 | 10/1994 |
| MX | PA99000033 | 9/2004 |

OTHER PUBLICATIONS

The North American Millers' Association, "Corn Milling Process", http://web.archive.org/web/20021121060729/http://www.namamillers.org/ci_products_corn_mill.html, Nov. 21, 2002, accessed Aug. 20, 2012.*

Fulmer, "Electricity-ethanol co-production from sugar cane: a technical and economic assessment", Princeton University master's thesis, Jan. 1991.*

Ma et al., "Biodiesel production: a review", Bioresource Technology 70:1-15 (1999).*

U.S. Appl. No. 60/838,642, filed Aug. 18, 2006 entitled "Kernel Fractionation Process".

U.S. Appl. No. 60/858,107, filed Nov. 10, 2006 entitled "Power Production Using Grain Fractionation Products".

Kleber, Mark, Mississippi Renewable Energy Conference—Mar. 25-26, 2003, mg engineering Lurgi PSI, Biodesel Capabilities, 2003, pp. 1-28.

Holcomb, Manuel, Harold C. Thompson Jr., Willie M. Cooper and Marvin L. Hopper. SFE Extraction of alfatoxins (B1, B2, G1, and G2) from corn and analysis by HPLC. The Journal of Supercritical Fluids, vol. 9 Issue 2, Jun. 1996, pp. 118-121.

Ronyai, E., B. Simandi, S. Tomoskozi, A. Deak, L. Vigh, and Zs. Weinbrenner. Supercritical fluid extraction of corn germ with carbon dioxide-ethyl alcohol mixture. The Journal of Supercritical Fluids, vol. 14 Issue 1, Oct. 1998, pp. 75-81.

Otles, Semih. Supercritical Fluids and Its Applications in Food Industry. http://eng.ege.edu.tr/~otles/SupercriticalFluids-ScienceAndTechnology/bolumb/Wc197588f62dd7.htm.

Taylor, Scott L. Jerry W. King, and Gary R. List. Determination of Oil Content in Oilseeds by Analytical Supercritical Fluid Extraction. JAOCS, vol. 70 Issue 4, Apr. 1993, pp. 437-439.

Kice Industries, Inc. web site, Multi-Aspirators, http://www.kice.com/products/multiaspirators/index.html, Mar. 19, 2007, seven total pages.

Kice Industries, Inc. web site, Bran Finisher, http://www.kice.com/products/branfinisher/index.html, Mar. 19, 2007, three total pages.

GBS Group, BI-MIX Intensive Dampener product brochure, Sangati Berga, Golfetto, Jun. 2002, three total pages.

GBS Group, Synthesis Rollermill product brochure, Sangati Berga, Golfetto, Jun. 2002, fourteen total pages.

Satake Corporation web site, Maize Degermer VBF product page and brochure, http:/www.satake.co.uk, Mar. 21, 2007, two total pages.

Forsbergs, Inc. web site, cutomer satisfaction page, P-Series Destoners product page, and Vacuum Gravityy Separator, http:/www.forsbergs,com, Mar. 21, 2007, seven total pages.

Great Western Manufacturing web site, "HS" Free Swinging Sifter product brochure, http:/www.gwmfg.com, Mar. 19, 2007, five total pages.

E. Reverchon, G. Della Porta, D. Gorgoglione. Supercritical $CO_2$ fractionation of jasmine concrete. J. Supercrit. Fluids 8 (1995) 60-65.

E. Reverchon, G. Della Porta. Rose concrete fractionation by supercritical $CO_2$. J. Supercrit. Fluids 9 (1996) 199-204.

R. L. Smith Jr., R.M. Malaluan, W.B. Setianto, H. Inomata, K. Arai. Separation of cashew (*Anacardium occidentale* L.) nut shell liquid with supercritical carbon dioxide. Biores. Technol. 88 (2003) 1-7.

M. A. Rostagno, J.M.A. Araujo, D. Sandi. Supercritical fluid extraction of isoflavones from soybean flour, Food Chem. 78 (2002) 111-117.

L. Sesti Osseo, G. Caputo, I. Gracia, E. Reverchon. Continuous fraction of used frying oil by supercritical CO2. J. Am. Oil Chem. Soc. (JAOCS) 81 (9) (2004) 879-885.

Alberto Bertucco, Francesco Sanmartin and Giuseppe Storti. Simulated moving bed technology for continuous, countercurrent solid-fluid supercritical extraction. The Journal of Supercritical Fluids, vol. 8, Issue 2, Jun. 1995, 138-148.

H. Lee, B.H. Chung and Y. Park. Concentration of tocopherols from soybean sludge by supercritical carbon dioxide. *JAOCS* 68 (1991), p. 571.

G. Brunner, Th. Malchow, K. Stürken and Th. Gottschau. Separation of tocopherols from deodorizer condensates by countercurrent extraction with carbon dioxide. *J. Supercrit. Fluids* 4 (1991), p. 72.

G. Brunner. Gas Extraction—An Introduction to Fundamentals of Supercritical Fluid and the Application to Separation Processes. Springer, Berlin (1994).

J.A. Briones, J.C. Mullins and M.C. Thies. Solvent extraction of fatty acids from natural oils with liquid water at elevated temperatures and pressures. *JAOCS* 67 (1990), p. 852.

P. Bondioli, C. Mariani, A. Lanzani, E. Fedeli and A. Muller. Squalene recovery from olive oil deodorizer distillates. *JAOCS* 70 (1993), p. 763.

O.J. Catchpole and J.C. von Kamp. Extraction of squalene from shark liver oil in a packed column using supercritical $CO_2$. *Ind. Eng. Chem. Res.* 36 (1997), p. 4318.

M.F. Mendes, F.L.P. Pessoa, G.V. Coelho, and A.M.C. Uller. Recovery of the high aggregated compounds present in the deodorizer distillate of vegetable oils using supercritical fluids. JAOCS 34:2, Jun. 2005, pp. 157-162.

D. D. Christianson, J. P. Friedrich, G. R. List, K. Warner, E. B. Bagley, A. C. Stringfellow, G. E. Inglett. Supercritical Fluid Extraction of Dry-Milled Corn Germ with Carbon Dioxide. Journal of Food Science 49 (1), 229-232.

(56) References Cited

OTHER PUBLICATIONS

B.M.C. Soares, F.M.C. Gamarra, L.C. Paviani, L.A.G. Goncalves, F.A. Cabral. Solubility of triacyclglycerols in supercritical carbon dioxide. J. Supercrit. Fluids. 2007, 6 total pages.

Ozlem Guclu-Ustundag, Feral Temelli. Correlating the solubility behavior of minor lipid components in supercritical carbon dioxide. J. of Supercritical Fluids 31 (2004) 235-253.

Helena Sovova, Marie Zarevucka, Miroslav Vacek, and Karel Stransky. Solubility of two vegetable oils in supercritical carbon dioxide. J. of Supercritical Fluids 20 (2001) pp. 15-28.

Masturah Markom, Harcharan Singh, and Masitah Hasan. Supercritical $CO_2$ fractionation of crude palm oil. J. of Supercritical Fluids 20 (2001) pp. 45-53.

\* cited by examiner

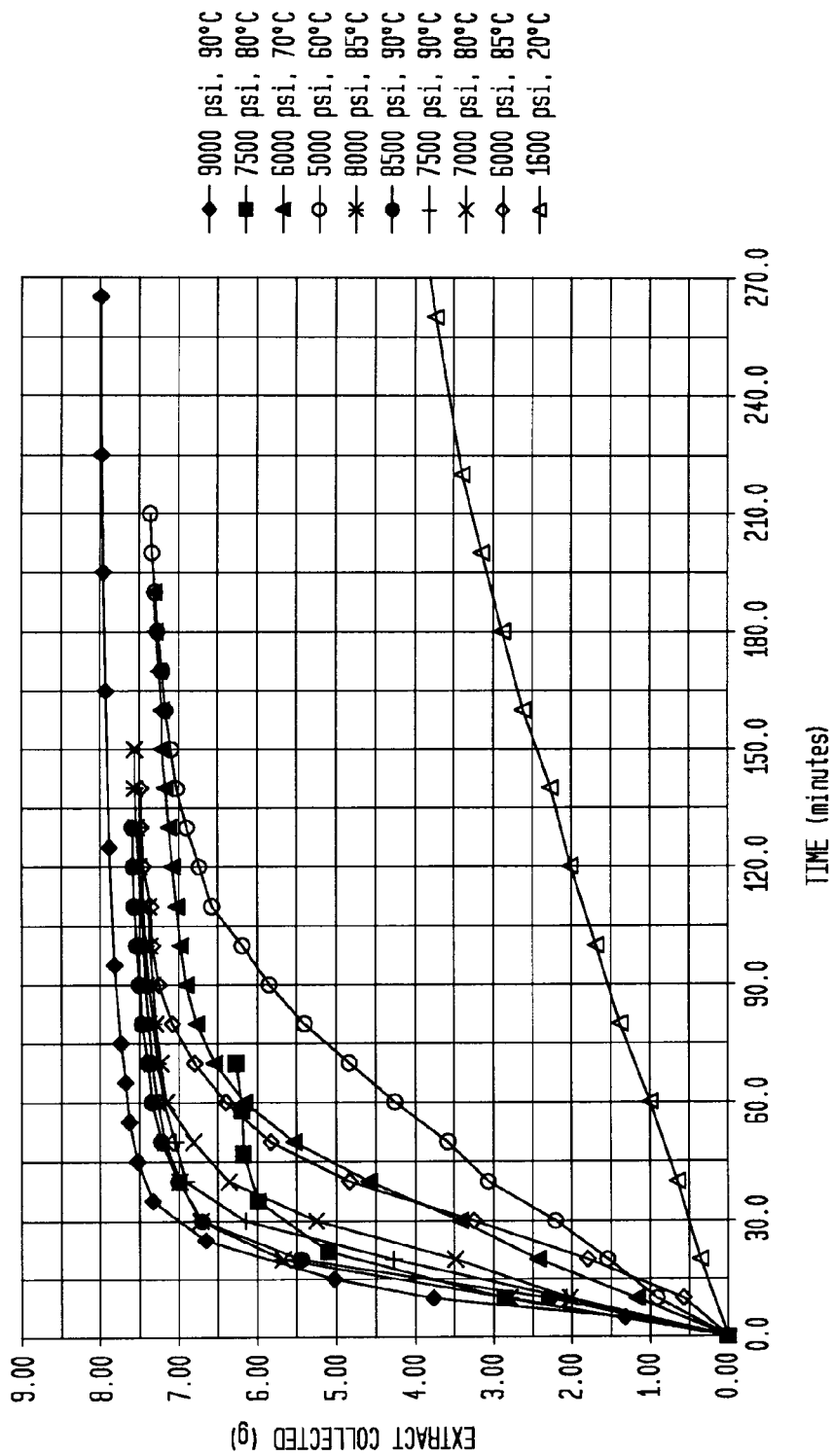

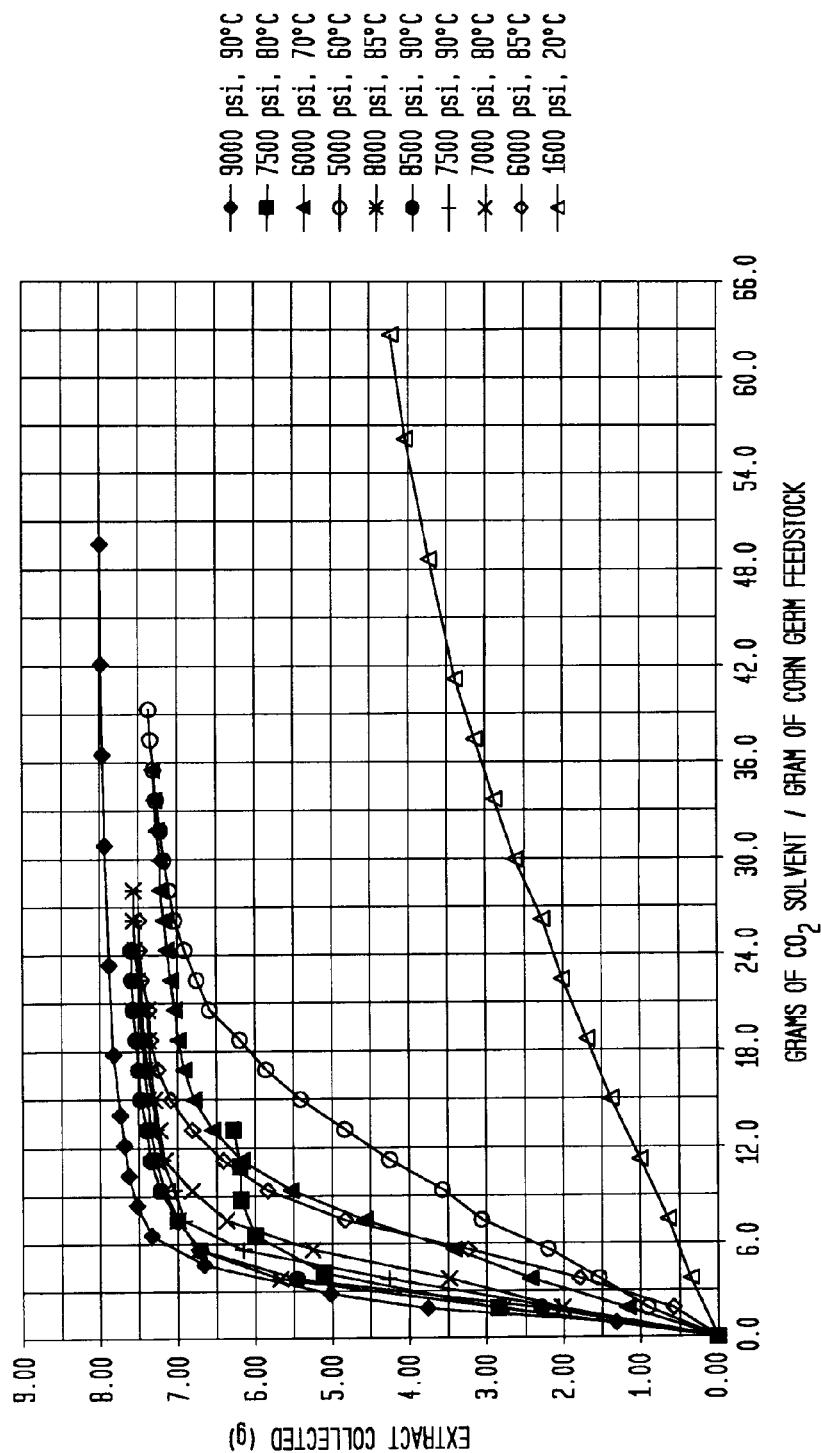

US 8,747,106 B2

POWER PRODUCTION USING GRAIN FRACTIONATION PRODUCTS

This application is the United States National Stage of Patent Corporation Treaty International Patent Application No. PCT/US06/45193, filed Nov. 22, 2006, which claims the benefit of U.S. Provisional Patent Application No. 60/838,642, filed Aug. 18, 2006, and U.S. Provisional Patent Application No. 60/858,107, filed Nov. 10, 2006, each hereby incorporated by reference herein.

I. TECHNICAL FIELD

A dry corn fractionation ethanol production system which utilizes at least one product of a dry corn fractionation process or ethanol production process as fuel to generate thermal energy for the production of ethanol. Specifically, thermal energy production devices and methods of generating thermal energy from dry corn fractionation co-products and fuel ethanol production co-products for the production of ethanol.

II. BACKGROUND

As shown in FIG. 1, conventional ethanol production systems (1) may mill whole corn (2) into a mixture of corn particles (3) (referred to hereinafter as "milled corn") which may include particles of corn bran, corn endosperm and corn germ. The milled corn (3) can be transferred to the ethanol production process (4) which includes the conventional steps of fermentation, distillation, and dehydration to generate an amount of ethanol (5). In the fermentation step, the milled corn (3) may be combined with an amount of water and an amount of alpha-amylase (or other enzyme capable of liquefying corn starch) to generate a mash in which the starch of the corn endosperm is liquefied. The mash may be held for a period of time at a temperature of between about 120 degrees Celsius (° C.) and about 150° C. to kill bacteria in the mash. The mash may then be held at a temperature of between about 90° C. and about 100° C. for a duration of time sufficient to achieve a desired level of liquefication of the starch. An amount of gluco-amylase (or other enzyme capable of generating fermentable sugars from the liquefied starch) added to the mash converts the liquefied starch to fermentable sugars, such as dextrose, in a process referred to as saccharification. Yeast can then be added to the mash to convert the sugars to an amount of ethanol (5) and an amount of, carbon dioxide (6) (or $CO_2$) along with other volatile organics. The amount of carbon dioxide (6) can be stored or sold in the marketplace. For sale in to certain markets or for certain applications, the amount of carbon dioxide (6) can be stripped of the other volatile organics and captured as an amount of purified carbon dioxide (9). The fermented mash often referred to as "beer" comprises an amount of ethanol (5) in a concentration of about eight percent to about twelve percent by weight, other liquids and non-fermentable solids. The amount of ethanol (5) in the beer can be separated and concentrated to about 190 proof by conventional distillation techniques and dehydrated by application to molecular sieve to produce a dehydrated ethanol of about 200 proof. The about 200 proof ethanol may be combined with up to about five percent denaturant to generate an amount of fuel grade ethanol (10).

The stillage which remains after distillation of the beer can comprise an amount of liquid typically referred to as "thin stillage" and an amount of remaining solids typically referred to as the "distillers grains". The thin stillage can be separated from the distillers grains (for example by centrifugation). The distillers grains can be dried by evaporation of the remaining thin stillage. The thin stillage can be concentrated by evaporation of water to generate a syrup containing about thirty percent solids (also referred to as "condensed distiller soluble"). The syrup can be recombined with the dried distillers grains to generate an amount of distillers dried grain with solubles (7) ("DDGS"). The DDGS can be sold as animal feed (8).

The amount of thermal energy (11) (or energy Btus or Btus) utilized by the conventional ethanol production process (4), including the steps of fermentation, distillation and dehydration, and by-product handling, which results in about a gallon of fuel ethanol (5), and a corresponding amount of DDGS (7) and carbon dioxide (6) utilizes an amount of thermal energy (11) of between about 30,000 and 40,000 British thermal units (hereinafter "Btu"). This amount of thermal energy (11) is typically generated by burning a corresponding amount of fossil fuel (12) such as oil, coal oil, coal or natural gas. In certain particular ethanol production processes (4), an amount of the DDGS (7) may be burned to produce a part of this amount of thermal energy as described by United States Patent Application No. 2003/0019736A1.

Even though there is an increasing demand for fuel ethanol (10) worldwide and an increasing amount of research in ethanol production, there remain substantial unresolved problems with respect to conventional ethanol production.

A first substantial problem with conventional ethanol production process as above-described may be that it requires the use of fossil fuel(s) in whole or in part to generate the amount of thermal energy required for the ethanol production process. One aspect of this problem can be that the cost of fossil fuels, such as coal or natural gas, may increase in disproportion to the price of being paid for the ethanol produced. Additionally, there may be spot shortages of gas and coal due to availability whether due to production, purification, or conveyance to the ethanol production facility.

A second substantial problem with conventional ethanol production process as above-described can be that for each 1.0 Btu equivalent of fuel consumed in conventional ethanol production only about 1.4 Btu to about 2.0 Btu equivalents of fuel ethanol may be produced.

A third substantial problem with conventional ethanol production process can be that there may be no manner of substantially reducing the amount of thermal energy consumed in the ethanol production process.

A fourth substantial problem with conventional ethanol production process can be that there may be no manner of substantially increasing the amount of ethanol produced by ethanol production plant having a fixed construction form using conventional ethanol production processes.

A fifth substantial problem with conventional ethanol production process can be that there may be that the market for the DDGS or carbon dioxide produced as by-products of the ethanol production process may be too small to consume all the DDGS or carbon dioxide produced by the conventional ethanol production facility.

III. DISCLOSURE OF INVENTION

Accordingly, a broad object of the invention can be to provide an ethanol production process (4) which can operate in a conventional fashion but without the use of any fossil fuels (12) such as gas or coal to generate the amount of thermal energy (11) required for fermentation, distillation, dehydration, and by-product handling to produce an amount of ethanol (5), or which substantially reduces the use of fossil fuel(s) (12) used to generate the amount of thermal energy (11) required for such fermentation, distillation, dehydration and by-product handling.

A second broad object of the invention can be to generate as part of an inventive milling process (13) or ethanol production process (4) a variety of fuels which can be burned to generate the amount of thermal energy (11) required by the ethanol production process (4) to produce an amount of ethanol (5).

A third broad object of the invention can be to provide an ethanol production process (4) but which operates in conventional fashion but utilizes a lesser amount of thermal energy (11) per unit of ethanol (5) produced. For example, an ethanol production process which for every 1.0 Btu consumed in the ethanol production process produces between about 2.0 Btu and about 2.8 Btu equivalents of ethanol.

A fourth broad object of the invention can be to provide an ethanol production process (4) which increases the amount of ethanol (5) produced without altering the constructional form of the ethanol production plant.

A fifth broad object of the invention can be to provide a utility for the by-products of the ethanol production process (4) even when there is no market in which to sell the by-products.

A sixth broad object of the invention can be to provide an ethanol production process which generates an amount of dried high protein corn gluten fraction (31) further described herein.

Naturally, further objects of the invention are disclosed throughout other areas of the specification, drawings, photographs, and claims.

IV. BRIEF DESCRIPTION OF THE DRAWINGS

FIG. 8 is a graph which plots extract collected in grams over time for carbon dioxide extraction of corn germ fraction at particular conditions of temperature and pressure.

FIG. 9 is a graph which plots extract collected in grams over grams of carbon dioxide per gram of corn germ feedstock.

V. MODE(S) FOR CARRYING OUT THE INVENTION

A dry corn fractionation ethanol production system which utilizes at least one product of a dry corn fractionation process or ethanol production process as a fuel to generate thermal energy for the production of ethanol.

Figure 1:
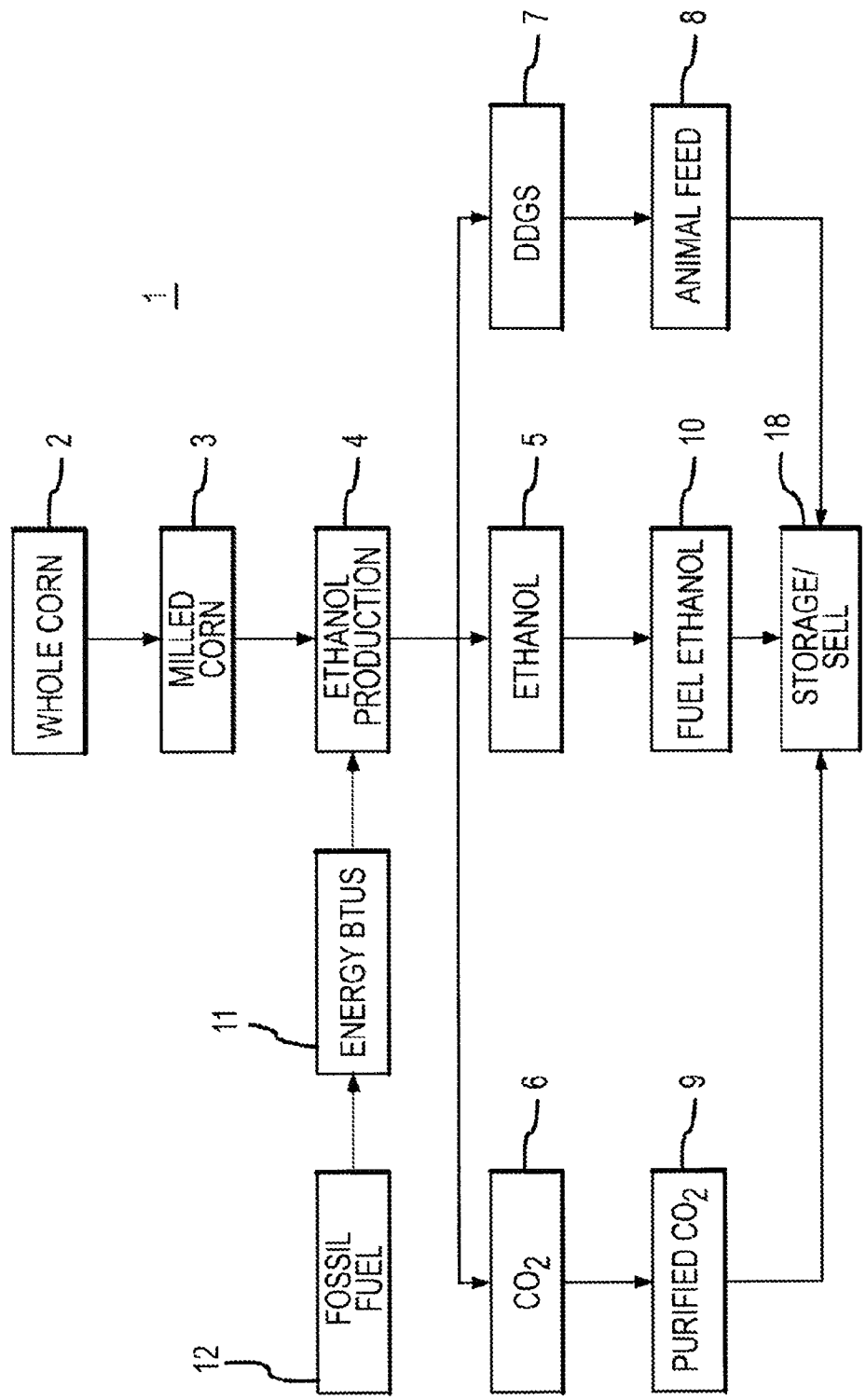
FIG. 1 is a flow diagram of the conventional fuel ethanol production technology.
Figure 2:
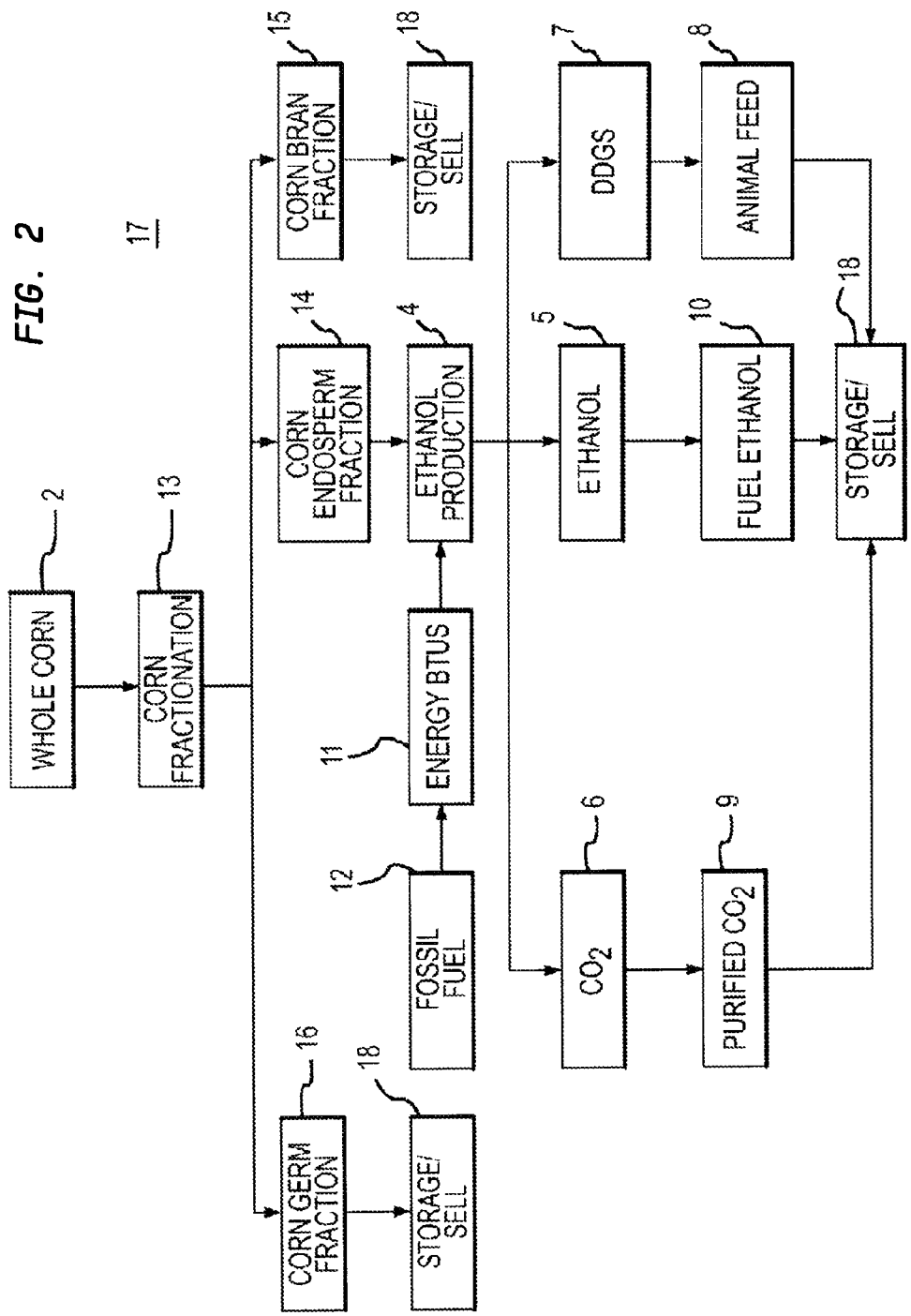
FIG. 2 is a flow diagram of a particular embodiment of the inventive fuel ethanol production technology utilizing grain fractionation products.

Now referring primarily to FIG. 2, which shows a first particular embodiment of an inventive dry corn fractionation ethanol production system (17). A dry corn fractionation process (13) can fracture whole corn kernels (2), typically number two whole corn (although other grades of whole corn can be used), into a mixture of corn particles which includes the constituent corn pericarp (often referred to as "corn bran"), corn germ, and corn endosperm and recovers from the mixture of corn particles at least two corn fractions at least one of which contains substantially all of the corn endosperm (hereinafter referred to as the "corn endosperm fraction" (14)) which can be introduced into the ethanol production process (4) (whether a conventional ethanol production process as above-described or otherwise) while the other fraction may comprise a corn bran fraction (15) or a corn germ fraction (16).

In the embodiment of the inventive dry corn fractionation ethanol production system (17) shown by FIG. 2, three corn fractions can be recovered from the mixture of corn particles which include a corn endosperm fraction (14), a corn bran fraction (15) and a corn germ fraction (16). A particular embodiment of the dry corn fractionation process (13) which can be utilized to produce these three corn fractions is described by U.S. Patent Application No. 60/838,642, hereby incorporated by reference herein. However, it is not intended that the inventive dry corn fractionation ethanol production system (17) described herein be limited to utilization of the particular corn fractionation process described therein and any manner of producing two corn fractions or three fractions from whole corn can be utilized with the various embodiments of the inventive dry corn fractionation ethanol production system (17) described herein or equivalents thereof.

In those embodiments of the inventive dry corn fractionation ethanol production system (17) which provides a corn fractionation process (13) which recovers three corn fractions the corn endosperm fraction (14) recovered can include mainly particles of corn endosperm. It is not intended however, that the corn endosperm fraction (14) be entirely comprised of the corn endosperm as the corn fractionation process (13) may not allow complete separation of all the corn bran or the corn germ from the corn endosperm fraction (14). As such, the corn endosperm fraction (14) may comprise a corn endosperm fraction (14) which has an increased endosperm content over an unfractionated mixture of corn particles or over milled corn as above-described or may comprise a fraction which is substantially all corn endosperm but which contains lesser amounts of corn bran or corn germ than contained in an unfractionated mixture of corn particles or milled corn.

The corn bran fraction (15) recovered can include mainly particles of corn bran. Again, it is not intended that the corn bran fraction (15) only include corn bran as a minor amount of corn endosperm or corn germ may be contained in the corn bran fraction (15). As such, the corn bran fraction (15) recovered may be substantially all corn bran but contains an amount of corn germ or corn endosperm of lesser amount than contained in the unfractionated mixture of corn particles. In the embodiment of the invention shown by FIG. 2, the corn bran fraction (15) can be placed in storage or sold in the market (18) as a source of fiber.

The corn germ fraction (16) recovered can include mainly particles of corn germ. Again, it is not intended that the corn germ fraction (16) only include corn germ as minor amounts of corn endosperm or corn bran may be contained in the fraction. As such, the corn germ fraction (16) recovered may be substantially all corn germ but may contain an amount of corn bran or corn endosperm of lesser amount than contained in the unfractionated mixture of corn particles or corn meal. In the embodiment of the invention shown by FIG. 2, the corn germ fraction (14) can be placed in storage stored or sold in the market (18).

The above-described corn endosperm fraction (14) can be further milled to generate particles of a desired or suitable size to be introduced into an otherwise conventional ethanol production process (4) such as above-described (or any manner of inventive ethanol production process) which utilizes fossil fuel (12) to generate the amount of thermal energy (11) utilized in the fermentation, distillation, dehydration and by-product handling steps. Importantly, the corn fractionation process (13) confers an advantage by providing a corn endosperm fraction (14) which can be milled to produce a mixture of particles having a substantially greater amount of corn endosperm per unit (whether by weight or volume) than the milled corn (3) conventionally introduced into the ethanol production process (4). Utilizing the particles resulting from milling the corn endosperm fraction (14) in the ethanol production process (4) can result in a substantial decrease in the amount of thermal energy (12) required to produce the same amount of ethanol (5) or fuel ethanol (10) as compared to using the above-described milled corn (3).

Now referring primarily to Table 1, thermal energy utilization data from conventional ethanol production systems (1) which utilize milled corn (3) as above-described as the fermentable material and the predicted thermal energy utilization data of the inventive dry corn fractionation ethanol production system (17) utilizing the above-described corn endosperm fraction (14) as the fermentable material are set out for an ethanol production plant having a fixed constructional form for a conventional ethanol production process (4).

TABLE 1

|  | Milled Corn | | Corn Endosperm Fraction | | |
| --- | --- | --- | --- | --- | --- |
|  | Btus per Gallon | Btus per Bushel | Btus per Gallon | Btus per Bushel | Percent Difference |
| Fermentation | 3,500 | 9,450 | 2,975 | 8,033 | 15 |
| Distillation and Dehydration | 14,000 | 37,800 | 11,900 | 32,130 | 15 |
| Concentration of Thin Stillage | 3,500 | 9,450 | 2,975 | 8,033 | 15 |
| Dry DDGS | 14,000 | 37,800 | 7,000 | 18,900 | 50 |
| Total | 35,000 | 94,500 | 24,850 | 67,095 | 29 |

As can be understood from Table 1, a significant reduction in amount of thermal energy (11) (shown as a comparison of Btus per gallon of ethanol (5) produced and as a comparison of the Btus consumed per bushel of number two corn processed) utilized whether by step in the ethanol production process (4) (showing a reduction of about 15% for the fermentation, distillation and dehydration, and concentration of thin stillage, and about 50% for the step of drying the DDGS (7)) or as to the total amount of thermal energy (11) consumed over the entire ethanol production process (4) (showing a reduction of about 29% over the entire ethanol production process) can be achieved by using a corn endosperm fraction (14) as the fermentable material as compared to conventional milled corn (3).

Naturally, the reduction in the amount of thermal energy (11) may vary and may on a unit by unit basis be lesser or greater than shown by the data; however, the use of a corn endosperm fraction (14) as above-described can achieve a substantial and important reduction in the amount of thermal energy (11) consumed in the ethanol production process (4) above-described or in other ethanol production processes which derive fermentable material from corn. Additionally, based on an overall reduction in Btus from about 35,000 Btus to about 24, 850 Btus (about a 29 percent reduction) the estimated amount of fuel energy returned per Btu consumed in the ethanol production process (4) is about 2.35 which is about a 70% increase in the amount of fuel energy returned per Btu in the same or similar ethanol production process (4) which utilizes milled corn as a fermentable material, being about 1.67.

Figure 3:
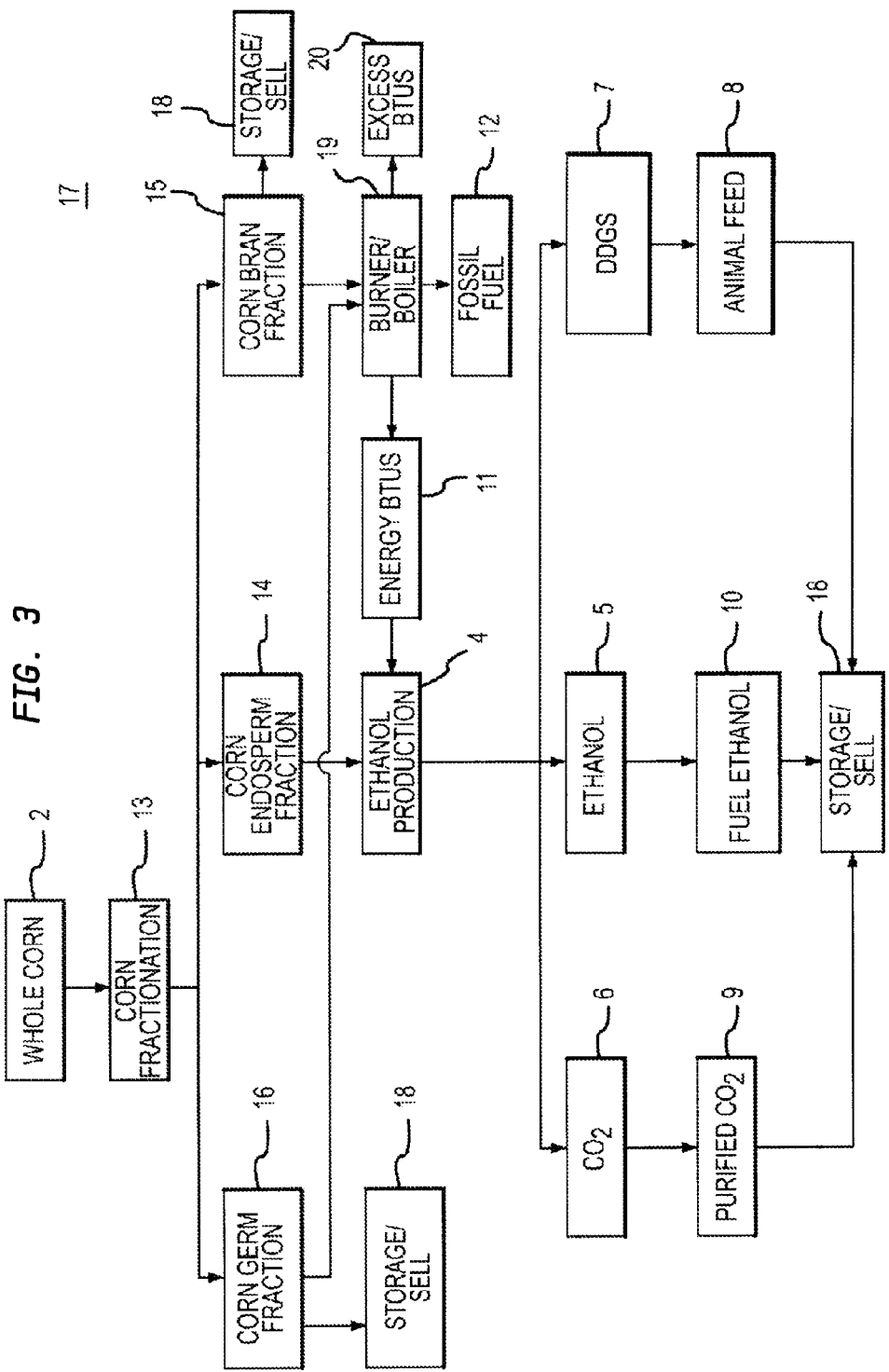
FIG. 3 is a flow diagram of a particular embodiment of the inventive fuel ethanol production technology utilizing grain fractionation products.

Now referring primarily to FIG. 3, a further particular embodiment of the inventive dry corn fractionation ethanol production system (17) can further include a burner (19) (or burner-boiler) capable of burning fossil fuels (12) such a natural gas or coal but further capable of burning an amount of the corn bran fraction (15) or the corn germ fraction (14), or each in various permutations or combinations, to produce the amount of thermal energy (11) (to use directly as heat for drying byproducts or to produce steam which can be used to heat mash, distill beer or the like) utilized in the ethanol production process (4). A burner (19) which can be utilized in accordance with this particular embodiment of the inventive dry corn fractionation ethanol production system or similar or equivalent embodiments of the inventive dry corn fractionation ethanol production system (17) can comprise a biomass co-fired burner which produces between 100,000 and 200,000 pph such as available for example by AGRA Industries, Inc., 1211 West Water Street, Merrill, Wisconsin 54424 USA which can be utilized to burn DDGS (7) but has not been prior shown to burn the corn bran fraction (15) or the corn germ fraction (16) or other fuels to provide the thermal energy (11) for the ethanol production process (4).

As to certain embodiments of the inventive dry corn fractionation ethanol production system (17) as shown in FIG. 3, the use of fossil fuels (12) such as natural gas or coal can be completely avoided by burning only the corn bran fraction (15) or only the corn germ fraction (16), or a combination of the corn bran fraction (15) and the corn germ fraction (16) to produce the amount of thermal energy (11) required for the ethanol production process (4).

Now referring primarily to Table 2 and Example 1 which sets out the total amount of thermal energy (10) which can be generated by burning the corn bran fraction (15) and the corn germ fraction (16).

TABLE 2

|  | Lbs/Bu | BTUs/lb | Total BTUs/Bu |
| --- | --- | --- | --- |
| Corn Bran Fraction | 3.4 | 7,952 | 27,037 |
| Corn Germ Fraction | 5.6 | 8,869 | 49,666 |
| Total |  |  | 76,703 |

As can be understood from Table 1 above, between about 24,850 Btus and about 35,000 Btus of thermal energy (11) can be utilized to produce one gallon of ethanol (4) depending on which fermentable material, such as milled corn (3) (about 35,000 Btus per gallon of ethanol (5)) or corn endosperm fraction (14) (about 24,000 Btus per gallon of ethanol (4)) (or other fermentable corn material), which enters the ethanol production process (4). From the data is summarized in Table 1, about 67,095 Btus are utilized in the ethanol production process (4) to process the corn endosperm fraction (14) from each bushel of number two corn (2) to yield about 2.7 gallons of ethanol (5) per bushel of whole corn (2) (the actual yield can vary between about 1.9 to about 2.9 gallons per bushel depending upon the ethanol production process utilized).

As can be understood from Table 2, if the entirety of the corn bran fraction (15) and the entirety of the corn germ fraction (16) obtained by the corn fractionation process (13) from a bushel of whole corn (2) can be burned in the burner (19) and the amount of thermal energy (11) generated can be about 76,703 Btus corresponding to the entirety or nearly the entirety of amount of thermal energy (11) required to process the corresponding amount corn endosperm fraction (14) from a bushel of whole corn (2) in the ethanol production process (4). As such, the use of any fossil fuel (12) in the ethanol production process (4) can be avoided when the inventive corn fractionation ethanol production system (17) is utilized; or the use of fossil fuel (12) can be substantially reduced in the conventional ethanol production process (1) utilizing milled corn. See also, Example 1.

Because the amount of thermal energy (11) generated from burning both the corn bran fraction (15) and the corn germ fraction (16) in the entirety can generate an excess amount of thermal energy (20) when the fermentable material is comprised entirely of corn endosperm fraction (14), the amount of corn bran fraction (15) and the amount of corn germ fraction (16) burned can be adjusted (whether by volume, proportion, or both) to match the thermal energy requirement of the ethanol production process (4) such that little or no excess amount of thermal energy (20) is produced and the unburned corn germ fraction (16) and the unburned corn bran fraction (15) can be placed in storage or sold in the market (18) to further offset the cost of the ethanol production process (4). Because both the corn bran fraction (15) and the corn germ fraction (16) can be utilized as fuels to generate substantial amounts of thermal energy (11) (20) which can either replace in the entirety or substantially reduce the amount of fossil fuel(s) (12) utilized to produce a unit of ethanol (5). Additionally, because the price of fossil fuel(s) (12) may fluctuate over time and because the price at which the corn germ fraction (16) and the corn bran fraction (15) can be sold may fluctuate over time the ratio of the corn germ fraction (16), the corn bran fraction (15), and various fossil fuels (12) burned to generate the amount of thermal energy (11) required for the ethanol production process (4) can be adjusted to minimize the cost per unit of fuel ethanol (5).

Figure 4:
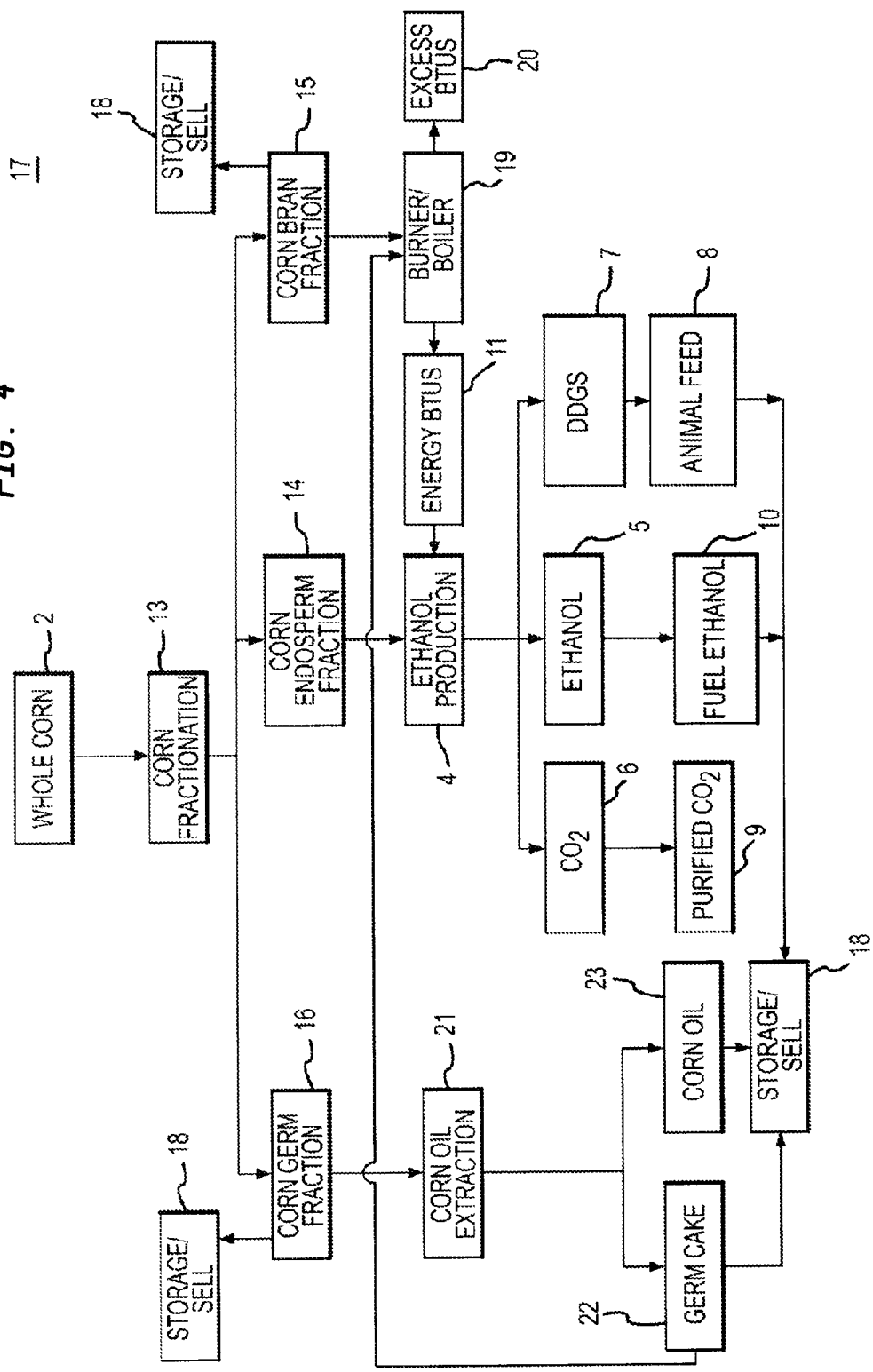
FIG. 4 is a flow diagram of a particular embodiment of the inventive fuel ethanol production technology utilizing grain fractionation products.

Now referring primarily to FIG. 4, a further particular embodiment of the inventive dry corn fractionation ethanol production system (17) can further include a corn oil extraction process (21) capable of extracting (or removing) an amount of corn oil (23) from an amount of the corn germ fraction (16) to generate an amount of germ cake (22). See as examples, U.S. patent application Ser. Nos. 6,201,142; 4,495,207; and 4,341,73, hereby incorporated by reference herein, although it is not intended that the inventive dry corn fractionation ethanol production system (17) be limited to any one of the technologies described therein. The amount of germ cake (22) and the amount of corn oil (23) can be placed in storage or sold in the market (18) as animal feed and food grade corn oil respectively. In the alternative, the amount of germ cake (22) (or a portion of the amount of germ cake (22)) can be burned in the burner (19) separately or in combination with an amount the corn bran fraction (15) to generate the amount of thermal energy (11) for the ethanol production process (4) as above-described for the corn germ fraction (16).

TABLE 3

| | Lbs/Bu | BTUs/lb | Total BTU/Bu |
|---|---|---|---|
| Corn Bran Fraction | 3.4 | 7,952 | 27,037 |
| Germ Cake | 4.3 | 6,495 | 27,928 |
| Corn Oil | 1.3 | 16,938 | 22,019 |
| Total | | | 76,984 |

As can be understood from Table 3, the amount of germ cake (22) when burned can generate a substantial amount of thermal energy (11) when burned (about 6,495 btus per pound based on remaining corn oil in the germ cake) with about 4.3 pounds of germ cake (22) produced per bushel of whole corn (2). The extracted corn oil (23) when burned can also generate a substantial amount of thermal energy (11) (about 16,000 btus per pound) with about 2.0 pounds of corn oil typically extractable from a bushel of whole corn (2). If the entirety of the corn bran fraction (15), the germ cake (22) and the corn oil (23) are burned in the burner (19) from each bushel of whole corn (2) introduced into the corn fractionation process (13), the amount of thermal energy (11) (about 76,984 btus) to process the corresponding amount of endosperm fraction (14) obtained from a bushel of whole corn (2) through the ethanol production process (4) can be generated and an excess of thermal energy (20) of about 9889 Btus can also be generated. Because an excess amount of thermal energy (20) can be generated, the amount of each of the corn bran fraction (17), the amount of germ cake (22), or the amount of corn oil (23) burned can be adjusted with more or less of each placed in storage or sold in the market (18) as food or animal feed. As to certain embodiments of the inventive dry corn fractionation ethanol production system (17), the amount of the corn bran fraction (15), the amount of germ cake (22), or the amount of corn oil (23) burned can be adjusted or continuously adjusted in various combinations to generate the amount of thermal energy (11) required without or with little excess thermal energy (20) generated.

Now referring to Table 4, which shows the relative Btu value of the germ cake (22) having different amounts of corn oil (23) remaining in the corn germ fraction (16). As can be understood from Table 4, the removal of the corn oil (23) from the corn germ fraction (16) (shown between 100% removal of corn oil in corn germ fraction and 0% removal of corn oil in corn germ fraction) reduces the amount of thermal energy (11) generated when the germ cake (22) burns. As such, by adjusting the amount of unextracted corn oil remaining in the germ cake (22), the amount of thermal energy (11) which can be generated by the germ cake (22) can be increased or decreased when burned.

TABLE 4

| % Total Corn Oil in Corn Germ Fraction | % wt. Corn Oil in Corn Germ Fraction | Btu Value of Remaining Corn Oil Per Pound Corn Germ Fraction | % wt. Corn Germ Fraction | Btu Value Per Pound of Corn Germ Cake | Total Btu Value Per Pound of Germ Cake |
|---|---|---|---|---|---|
| 0 | 0 | 0 | 100.00 | 6495.05 | 6495.05 |
| 10 | 2.34 | 396.86 | 97.66 | 6343.07 | 6739.93 |
| 20 | 4.69 | 793.72 | 95.31 | 6190.43 | 6984.15 |
| 30 | 7.03 | 1190.57 | 92.97 | 6038.45 | 7229.02 |
| 40 | 9.37 | 1587.43 | 90.63 | 5886.46 | 7473.89 |
| 50 | 11.76 | 1984.29 | 88.24 | 5731.23 | 7715.52 |
| 60 | 14.96 | 2533.59 | 85.04 | 5523.39 | 8056.98 |
| 70 | 16.40 | 2778.00 | 83.60 | 5429.86 | 8207.86 |
| 80 | 18.74 | 3174.86 | 81.26 | 5277.88 | 8452.74 |

TABLE 4-continued

| % Total Corn Oil in Corn Germ Fraction | % wt. Corn Oil in Corn Germ Fraction | Btu Value of Remaining Corn Oil Per Pound Corn Germ Fraction | % wt. Corn Germ Fraction | Btu Value Per Pound of Corn Germ Cake | Total Btu Value Per Pound of Germ Cake |
|---|---|---|---|---|---|
| 90 | 21.99 | 3724.16 | 78.01 | 5066.79 | 8790.95 |
| 100 | 23.43 | 3895.74 | 76.57 | 4973.26 | 8869.00 |

The values shown in Table 4 are based on an estimated highest amount of corn oil in the corn germ as 23.43% by weight. See Example 2 which shows this as the highest recovery by weight percent from the corn germ fraction (16). The values are also based on a Btu value of 8869.0 Btus per pound of the corn germ fraction (16) and 16,938 Btus per pound of extracted corn oil (23). See also Example 1.

Again referring primarily to FIG. 4, in a particular embodiment of the inventive dry corn fractionation ethanol production system (17), the amount of unextracted oil in the germ cake (22) can be adjusted such that the sum of the amount of thermal energy generated by burning the entirety of the corn bran fraction (15) and the amount of thermal energy generated by burning the entirety of the germ cake (22) with the adjusted amount of unextracted oil can correspond to the amount of thermal energy (11) required in the ethanol production process (4).

Figure 5:
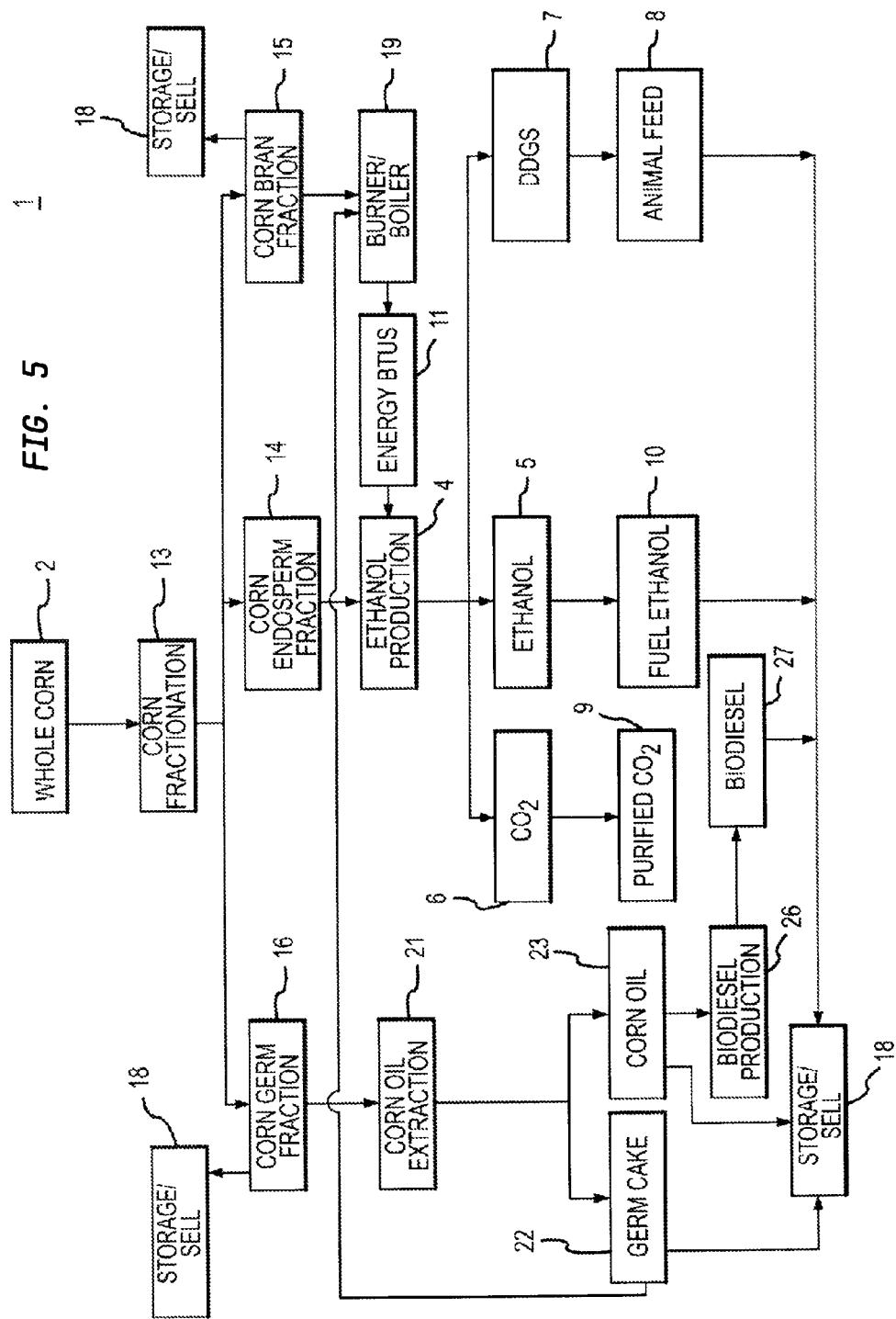
FIG. 5 is a flow diagram of a particular embodiment of the inventive fuel ethanol production technology utilizing grain fractionation products.

Now referring primarily to FIG. 5, another particular embodiment of the inventive dry corn fractionation ethanol production system (17) can further include a biodiesel production process (26) which can convert the amount of corn oil (23) extracted or removed from the corn germ (16) into an amount of biodiesel (27) which can be stored or sold in the marketplace (18). See for example the description of biodiesel production Martin Kleber, "Mississippi Renewable Energy Conference" (2003), hereby incorporated by reference herein. However, it is not intended that the devices or methods of producing biodiesel (27) described in the reference be limiting to the various devices and methods which can be utilized with the invention for the production of biodiesel (27).

Figure 6:
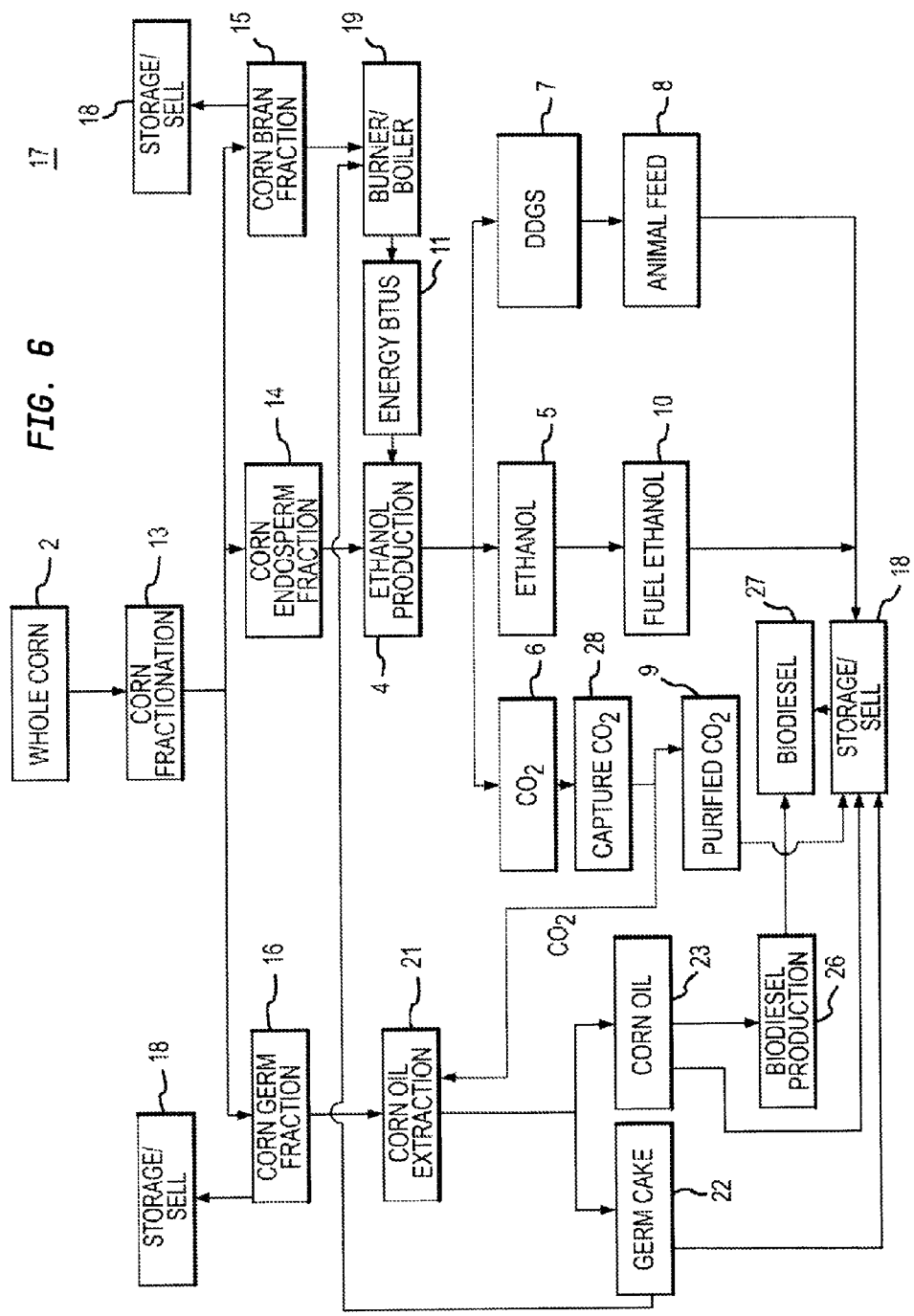
FIG. 6 is a flow diagram of a particular embodiment of the inventive fuel ethanol production technology utilizing grain fractionation products.

Now referring primarily to FIG. 6, a particular embodiment of the inventive dry corn fractionation ethanol production system (17) as above-described can further include a carbon dioxide capture process (28) which establishes the amount of carbon dioxide (6) produced by the ethanol production process (4) at pressures and temperatures useful in the corn oil extraction process (21) which removes or extracts all or a part of the corn oil (23) from the corn germ fraction (14) by carbon dioxide extraction.

Now referring to FIGS. 8 and 9 and Example 2 which sets out a plurality of conditions and results for carbon dioxide extraction of the corn germ fraction (16) and which provides a comparison graph of the amount of corn oil (23) generated over time at various conditions described in Example 2, it can be understood that an amount of corn oil (23) can be extracted or removed from an amount of the corn germ fraction (16) by fluidicly engaging an amount of carbon dioxide (6) (fluidicly encompassing either the liquid or the gas phase of carbon dioxide, or both, depending upon the temperature and pressure delivered and whether delivered in a continuous, varied, pulsed, or other mode) from the carbon dioxide capture process (28) with the amount of corn germ fraction (14) over a broad range of temperatures, pressures, and carbon dioxide flow rates.

Again referring primarily to FIGS. 8 and 9 and Example 2, it can be understood for example that at a particular flow rate of the amount of carbon dioxide (6) fluidicly engaged with a particular amount of corn germ fraction (16) an amount of corn oil (23) can be extracted or removed from the corn germ fraction (16) over a broad range of carbon dioxide pressures such as between about 1,000 pounds per square inch ("psi") and about 10,000 psi. As shown by trials 1-10 and FIGS. 8 and 9, as the carbon dioxide pressure increases the amount of corn oil (23) the amount of corn oil (expressed in grams) removed from the amount of corn germ fraction (16) can increase and the extraction rate (expressed as grams corn oil per unit time) can also increase. While it appears that the pressure at which carbon dioxide fluidicly engages the amount of corn germ may be preferable above about 5000 psi, or between about 5000 psi and about 9000 psi, or even more preferred between about 6000 psi and about 9000 psi, or even more preferred at or about 9000 psi, it is not intended that the invention be limited to one carbon dioxide pressure or a narrow range of carbon dioxide pressure within the broad range above-described. Rather, the numerous examples of the carbon dioxide pressures at which corn oil can be extracted from the corn germ fraction are intended to provide the person of ordinary skill in the art sufficient description to practice the various embodiments of the inventive dry corn fractionation ethanol production system (17) which may necessitate adjustment of the amount of corn oil extracted or the rate at which the amount of corn oil (23) is extracted from the amount of corn germ fraction (16). As such, the pressure at which a part of the amount of carbon dioxide (6) fluidicly engages the amount of corn germ fraction (16) or amount of corn oil (23) in the corn oil extraction process (21) can comprise a range of pressures including a range of pressure of between about 1000 pounds per square inch (psi) and about 10,000 psi, a range of pressure of between about 4000 psi and about 10,000 psi, a range of pressure of between about 5000 psi and about 10,000 psi, a range of pressure of between about 6000 psi and about 10,000 psi, a range of pressure of between about 7000 psi and about 10,000 psi, a range of pressure of between about 8000 psi and about 10,000 psi, a range of pressure of between about 9000 psi and about 10,000 psi, a range of pressure of between about 5000 psi and about 9,000 psi, a range of pressure of between about 6,000 psi and about 9,000 psi, a range of pressure of between about 7000 psi and about 9,000 psi, a range of pressure of between about 8000 psi and about 9,000 pounds psi, a range of pressure of between about 5000 psi and about 8,000 pounds psi, a range of pressure of between about 6000 psi and about 8,000 pounds psi, and a range of pressure of between about 7000 psi and about 8,000 pounds psi.

Additionally, extraction of an amount of corn oil (23) with an amount of carbon dioxide (6) can be achieved over a wide range of temperature such as between about 20 degrees centigrade (° C.) and about 90° C. As shown, the amount of corn oil (23) (expressed in grams) removed from the amount of corn germ fraction can increase and the extraction rate (expressed as grams corn oil per unit time) can also increase as temperature increases. Again, while it may appear to be more preferable to fluidicly engage the amount of carbon dioxide (6) with the amount of corn germ fraction (16) at temperatures above about 60° C., or within a range of between about 60° C. and about 90° C., or within a range of between about 85° C. and about 90° C., it is not intended that the invention be limited to one carbon dioxide temperature or a narrow range of carbon dioxide temperatures within the broad range above-described. Rather, the numerous examples of the carbon dioxide temperatures at which corn oil can be extracted from the corn germ fraction are intended to provide the person of ordinary skill in the art sufficient description to practice the various embodiments of the inventive dry corn fractionation ethanol production system (17) which may necessitate adjustment of the amount of corn oil extracted or the rate at which the amount of corn oil (23) is extracted from the amount of corn germ fraction (16).

Similarly, the flow rate of the amount of carbon dioxide (6) captured fluidicly engaged with the amount of corn germ fraction (16) can be adjusted depending on the amount of carbon dioxide captured, the rate at which the amount of carbon dioxide can be conditioned to the desired pressure or temperature, the amount of corn germ fraction fluidicly engaged with the conditioned amount of carbon dioxide (6), the relative proportion of the amount of extracted corn oil (23) to the amount of unextracted corn oil to remain in the corn germ fraction (16), or the like.

Figure 7:
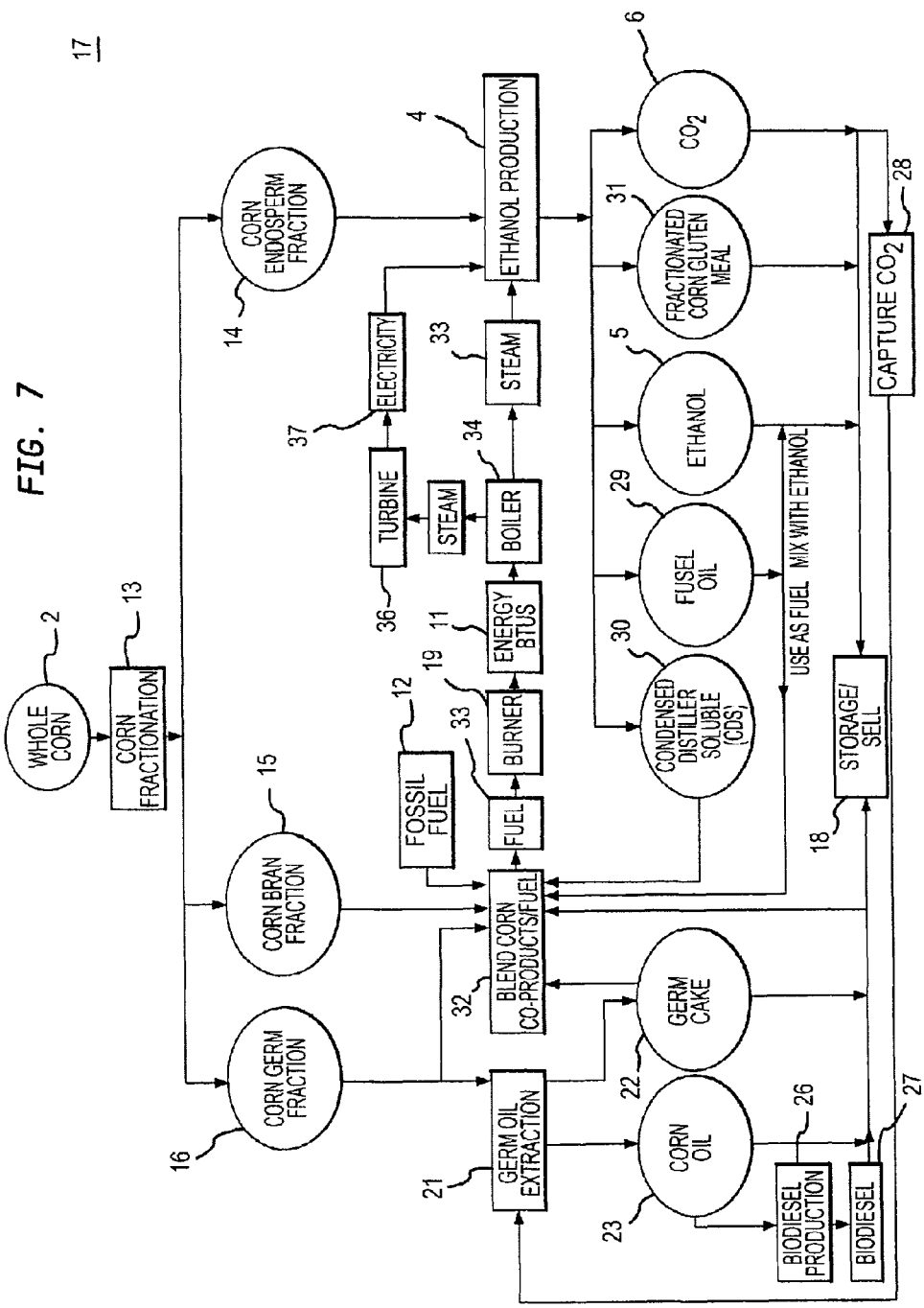
FIG. 7 is a flow diagram of a particular embodiment of the inventive fuel ethanol production technology utilizing grain fractionation products.

Now referring primarily to FIG. 7, a particular embodiment of the inventive dry corn fractionation ethanol production system (17) can further include an amount of fusel oil (29). The amount of fusel oil (29) (also referred to as "fusel alcohols") are higher order alcohols (greater than two carbon) formed during fermentation of fermentable material such as an amount of corn meal (3) or an amount of corn endosperm fraction (14). The compounds encompassed by the term fusel oil (29) include chiefly 1-propanol, 2-propanol, butanol (of various isomers), amyl alcohol, and furural individually or combined in various proportion depending on fermentation conditions such as temperature, pH, nitrogen content, or yeast activity. During distillation, fusel oils (29) are concentrated in the "tails" at the end of the distillation process. Because fusel oil (29) can be almost completely separated, or separated to a desired extent, by reflux distillation, an amount of fusel oil (29) can be separated from the amount of ethanol (5) and transferred to the burner (19) and burned as a fuel to generate a part of the amount of thermal energy (11) utilized in the ethanol production process (4) above-described. Alternately, the fusel oil (29) can be mixed with or remain a part of the amount of ethanol (5). As shown in Table 5, the amount of fusel oil (29) can yield about 12,000 Btus per pound or about 2,400 Btus per bushel of whole corn (2) processed in the corn fractionation process (12).

TABLE 5

|  | Lbs/Bu | BTUs/lb | Total BTUs/Bu |
|---|---|---|---|
| Fusel Oil | 0.2 | 12,000 | 2,400 |
| Condensed Distiller Soluble (CDS) | 2.06 | 4,000 | 8,240 |
| Total | 2.08 | 16,000 | 10,640 |

Again referring primarily to FIG. 7, a particular embodiment of the inventive dry corn fractionation ethanol production system (17) can utilize an amount of condensed distiller soluble (CDS) (30) (also referred to above as "syrup" from condensing the thin stillage in the ethanol production process (4)) as a fuel which can be burned in the burner (19) to generate a part of the amount of thermal energy (11) utilized in the ethanol production process (4). As shown in Table 4, about 4,000 BTUs can be generated from each pound of CDS or about 8,240 BTUs from the CDS produced from each corresponding bushel of whole corn (2) introduced into the corn fractionation process (12).

Also, because certain embodiments of the inventive corn fractionation ethanol production system (17) introduce only the corn endosperm fraction (14) into the ethanol production process (4) and because the thin stillage or the CDS (30) when used as a fuel is not combined with the solids remaining from the fermentation of the corn endosperm fraction (14) another by product of the ethanol production process (4) can be a fractionated corn gluten meal (31) which can be dried and placed in storage or sold in the market (18) for as a very high protein animal feed.

A particular embodiment of the inventive dry corn fractionation ethanol production system (17) can further include a fuel blender (32) which can combine at least two fuels which the burner (19) burns to produce said amount of thermal energy (10) including, but not limited to the above-described corn bran fraction (15), corn germ fraction (16), corn germ cake (22), extracted corn oil (23), biodiesel (27), fusel oil (29), condensed distiller soluble (30), ethanol (5), fossil fuels (12) such as natural gas or coal. The fuel blender (32) can further selectably adjust the ratio between two or more fuels burned to establish a correspondence or match between the thermal energy produced with the amount of thermal energy (11) utilized in the ethanol production process (4) to avoid the production of excess thermal energy (20). A fuel feeder (33) can be coupled to the fuel blender (32) which adjusts the amount of the combined at least two fuels transferred to the burner (19) over a duration of time to produce the amount of thermal energy (11) during such duration of time required by the ethanol production process (4).

Another particular embodiment of the inventive dry corn fractionation ethanol production system (17) can further include a boiler (34) which receives the amount of thermal energy (34) to generate an amount of steam (35). The steam (35) can be utilized to transfer the amount of thermal energy (11) to the ethanol production process (4) or can be operably coupled to a turbine (36) for the production of an amount of electricity (37) which can be converted to the amount of thermal energy (11) utilized in the ethanol production process (4) or can be used to power any manner of electrical device, such as lights, motors, heaters, transfer pumps, or the like.

EXAMPLE 1

Heat of Combustion for Corn Derived Samples

The gross heat of combustion ($Q_g$ (gross)) hereafter designated as $Q_g$ was conducted under thirty (30) atmospheres of $O_2$ with a 1341 Oxygen Bomb calorimeter (Parr Instruments). Measurements and data reduction were conducted in accord with the guidelines of ASTM D 4809[(2)]. The $Q_g$ and net heat of combustion ($Q_n$) are related by equations 1-4.

$$Q_g(\text{gross}, t° \text{ C.}) = \frac{t \cdot W - e_1 - e_2 - e_3 - e_4}{1000 \text{ m}} \quad (1)$$

$$Q_g(\text{gross}, 25° \text{ C.}) = Q_g(\text{gross}, t° \text{ C.}) + A(t - 25) \quad (2)$$

$$t = t_c - t_a - r_1(b - a) - r_2(c - b) \quad (3)$$

$$Q_n(\text{net}, 25° \text{ C.}) = Q_g(\text{gross}, 25° \text{ C.}) - 0.2122xH \quad (4)$$

Definitions of the terms in equations 1-4 and the combustion data for each sample are given in Tables 6-9. The calorimeter energy equivalent factor was determined from combustion of benzoic acid certified against NIST Standard Reference Material (SRM) 39j[(3)].

TABLE 6

Combustion Data - Corn Germ Fraction (16).

| Data Description and Symbol | Data |
|---|---|
| Time (min) of firing: a | 6.3 |
| Time (min) for 60% of total temperature rise: b | 7.8 |
| Time (min) after the temperature rise in which the rate of rise is constant: c | 13 |
| Temperature (° C.) at time a: $t_a$ | 23.402 |
| Temperature (° C.) at time c: $t_c$ | 25.402 |
| Temperature Rise: t | 2.016 |
| Rate (° C. min$^{-1}$) of pre-ignition temperature rise: $r_1$ | 0.0012 |
| Rate (° C. min$^{-1}$) of temperature rise during post-ignition period: $r_2$ | −0.0035 |
| Standard NaOH (mL) for HNO$_3$ acid neutralization: $c_1$ | 6.9 |
| Normality of Standard NaOH | 0.1050 |
| Sulfur (%) in sample: $c_2$ | 0.0 |
| Fuse wire (cm) consumed in firing: $c_3$ | 7.3 |
| Hydrogen (mass %) in sample: H | 5.0 |
| Mass(g) of sample: $m_c$ | 0.9974 |
| Correction (J) for heat of formation of HNO$_3$: $e_1$ | 43.4 |
| Correction (J) for heat of formation of H$_2$SO$_4$: $e_2$ | 0 |
| Correction (J) for heat of combustion of fuse wire: $e_3$ | 70.3 |
| Energy Equivalent Factor: W (J° C.$^{-1}$) | 10259.3 |
| Gross Heat of Combustion (MJ kg$^{-1}$): $Q_g$ (gross, t ° C.) | 20.633 |
| Heat capacity (MJ kg$^{-1}$° C.$^{-1}$) correction: A | −0.0077 |
| Gross Heat of Combustion at Constant Volume (MJ kg$^{-1}$): $Q_g$ (gross, 25° C.) | 20.630 |
| Net Heat of Combustion at Constant Pressure (MJ kg$^{-1}$): $Q_n$ (gross, 25° C.) | 19.574 |
| % Ash | 3.1 |

File: 091306
Environmental Conditions: 23° C./54% RH
% Hydrogen: assumed value

TABLE 7

Combustion Data - Corn Germ Extract Residue (22).

| Data Description and Symbol | Data |
|---|---|
| Time (min) of firing: a | 6.3 |
| Time (min) for 60% of total temperature rise: b | 7.8 |
| Time (min) after the temperature rise in which the rate of rise is constant: c | 13 |
| Temperature (° C.) at time a: $t_a$ | 22.718 |
| Temperature (° C.) at time c: $t_c$ | 24.437 |
| Temperature Rise: t | 1.717 |
| Rate (° C. min$^{-1}$) of pre-ignition temperature rise: $r_1$ | 0.0039 |
| Rate (° C. min$^{-1}$) of temperature rise during post-ignition period: $r_2$ | −0.0012 |
| Standard NaOH (mL) for HNO$_3$ acid neutralization: $c_1$ | 6.5 |
| Normality of Standard NaOH | 0.1050 |
| Sulfur (%) in sample: $c_2$ | 0.0 |
| Fuse wire (cm) consumed in firing: $c_3$ | 9.5 |
| Hydrogen (mass %) in sample: H | 5.0 |
| Mass(g) of sample: $m_c$ | 1.0369 |
| Correction (J) for heat of formation of HNO$_3$: $e_1$ | 43.4 |
| Correction (J) for heat of formation of H$_2$SO$_4$: $e_2$ | 0 |
| Correction (J) for heat of combustion of fuse wire: $e_3$ | 91.5 |
| Energy Equivalent Factor: W (J° C.$^{-1}$) | 10259.3 |
| Gross Heat of Combustion (MJ kg$^{-1}$): $Q_g$ (gross, t ° C.) | 16.867 |
| Heat capacity (MJ kg$^{-1}$° C.$^{-1}$) correction: A | −0.0092 |
| Gross Heat of Combustion at Constant Volume (MJ kg$^{-1}$): $Q_g$ (gross, 25° C.) | 16.872 |
| Net Heat of Combustion at Constant Pressure (MJ kg$^{-1}$): $Q_n$ (gross, 25° C.) | 15.811 |
| % Ash | 3.6 |

File: 091406
Environmental Conditions: 23° C./55% RH
% Hydrogen: assumed value

TABLE 8

Combustion Data - Raw Material Corn Bran Fraction (15).

| Data Description and Symbol | Data |
|---|---|
| Time (min) of firing: a | 6.3 |
| Time (min) for 60% of total temperature rise: b | 8.0 |
| Time (min) after the temperature rise in which the rate of rise is constant: c | 13 |
| Temperature (° C.) at time a: $t_a$ | 22.798 |
| Temperature (° C.) at time c: $t_c$ | 24.677 |
| Temperature Rise: t | 1.885 |
| Rate (° C. min$^{-1}$) of pre-ignition temperature rise: $r_1$ | 0.0008 |
| Rate (° C. min$^{-1}$) of temperature rise during post-ignition period: $r_2$ | −0.0016 |
| Standard NaOH (mL) for HNO$_3$ acid neutralization: $c_1$ | 4.9 |
| Normality of Standard NaOH | 0.1050 |
| Sulfur (%) in sample: $c_2$ | 0.0 |
| Fuse wire (cm) consumed in firing: $c_3$ | 7.3 |
| Hydrogen (mass %) in sample: H | 5.0 |
| Mass(g) of sample: $m_c$ | 1.0397 |
| Correction (J) for heat of formation of HNO$_3$: $e_1$ | 43.4 |
| Correction (J) for heat of formation of H$_2$SO$_4$: $e_2$ | 0 |
| Correction (J) for heat of combustion of fuse wire: $e_3$ | 70.3 |
| Energy Equivalent Factor: W (J° C.$^{-1}$) | 10259.3 |
| Gross Heat of Combustion (MJ kg$^{-1}$): $Q_g$ (gross, t ° C.) | 18.493 |
| Heat capacity (MJ kg$^{-1}$° C.$^{-1}$) correction: A | −0.0085 |
| Gross Heat of Combustion at Constant Volume (MJ kg$^{-1}$): $Q_g$ (gross, 25° C.) | 18.496 |
| Net Heat of Combustion at Constant Pressure (MJ kg$^{-1}$): $Q_n$ (gross, 25° C.) | 17.435 |
| % Ash | — |

File: 091506
Environmental Conditions: 23° C./55% RH
% Hydrogen: assumed value

TABLE 9

Combustion Data - Corn Germ Extract (21).

| Data Description and Symbol | Data |
|---|---|
| Time (min) of firing: a | 6.3 |
| Time (min) for 60% of total temperature rise: b | 7.8 |
| Time (min) after the temperature rise in which the rate of rise is constant: c | 13 |
| Temperature (° C.) at time a: $t_a$ | 22.731 |
| Temperature (° C.) at time c: $t_c$ | 26.347 |
| Temperature Rise: t | 3.632 |
| Rate (° C. min$^{-1}$) of pre-ignition temperature rise: $r_1$ | 0.0027 |
| Rate (° C. min$^{-1}$) of temperature rise during post-ignition period: $r_2$ | −0.0040 |
| Standard NaOH (mL) for HNO$_3$ acid neutralization: $c_1$ | 9.1 |
| Normality of Standard NaOH | 0.1050 |
| Sulfur (%) in sample: $c_2$ | 0.0 |
| Fuse wire (cm) consumed in firing: $c_3$ | 5.2 |
| Hydrogen (mass %) in sample: H | 5.0 |
| Mass(g) of sample: $m_c$ | 0.9436 |
| Correction (J) for heat of formation of HNO$_3$: $e_1$ | 43.4 |
| Correction (J) for heat of formation of H$_2$SO$_4$: $e_2$ | 0 |
| Correction (J) for heat of combustion of fuse wire: $e_3$ | 50.1 |
| Energy Equivalent Factor: W (J° C.$^{-1}$) | 10259.3 |
| Gross Heat of Combustion (MJ kg$^{-1}$): $Q_g$ (gross, t ° C.) | 39.398 |
| Heat capacity (MJ kg$^{-1}$° C.$^{-1}$) correction: A | 8.025E−5 |
| Gross Heat of Combustion at Constant Volume (MJ kg$^{-1}$): $Q_g$ (gross, 25° C.) | 39.398 |
| Net Heat of Combustion at Constant Pressure (MJ kg$^{-1}$): $Q_n$ (gross, 25° C.) | 38.337 |
| % Ash | — |

File: 091506
Environmental Conditions: 23° C./54% RH
% Hydrogen: assumed value

Results:

Table 10 summarizes derived values for $Q_g$ and $Q_n$. The estimated uncertainty for $Q_g$ is ±0.25%; uncertainty was based on ±σ where σ is the standard deviation for the energy equivalent factor (W=10259.3±23 J° C.$^{-1}$). The following observations apply to the computed values for $Q_g$ and $Q_n$ given in Table 9 and 10:

TABLE 10

Gross Heat of Combustion At Constant Volume.

| Sample | Gross Heat of Combustion at Constant Volume (25° C.) | | | |
|---|---|---|---|---|
| | cal g$^{-1}$ | J g$^{-1}$ | MJ kg$^{-1}$ | Btu lb$^{-1}$ |
| Raw Material Corn Germ | 4927.4 | 20630 | 20.630 | 8869 |
| | (4675.2) | (19574) | (19.574) | (8415) |
| Corn Germ Extract Residue | 4029.8 | 16872 | 16.872 | 7254 |
| | (3776.4) | (15811) | (15.811) | (6798) |
| Raw Material Corn Bran | 4417.7 | 18496 | 18.496 | 7952 |
| | (4164.3) | (17435) | (17.435) | (7496) |
| Corn Germ Extract | 9410.1 | 39398 | 39.398 | 16938 |
| | (9156.6) | (38337) | (38.337) | (16482) |

Note:
Parenthetical entries in columns 2-4 are estimates for $Q_n$ based on equation 4 and the assumption of 5 wt. % hydrogen.
Conversion Factors:
1 cal (International Table calorie) = 4.1868 J
1 Btu (British thermal unit) = 1055.06 J
1 cal (I.T.) g$^{-1}$ = 0.0041868 MJ kg$^{-1}$
1 Btu lb$^{-1}$ = 0.002326 MJ kg$^{-1}$ Summary: Table 11 sets out the summary of combustion data showing Btu Values derived for various corn fractions.

TABLE 11

Summary of Combustion Data.
BTU Values

| Material | Calories/Gram | Joules/Gram | Mega Joules/Kilogram | BTUs/lb. |
|---|---|---|---|---|
| Corn Germ (16) | 4,927.4 | 20,630 | 20.630 | 8,869 |
| Germ Cake (22) | 4,029.8 | 16,872 | 16.872 | 7,254 |
| Corn Bran (15) | 4,417.7 | 18,496 | 18.496 | 7,952 |
| Corn Oil (23) | 9,410.1 | 39,398 | 39.398 | 16,938 |

The raw material corn germ fraction (16) and the corn germ cake (22) both exhibited small ash residues at completion of the combustion process. The ash had the appearance expected for inorganic oxides. Ash was not observed for either the corn bran (15) or corn oil (23) samples.

The hydrogen content of the samples is unknown. Values for $Q_n$ were estimated with the assumption that each sample contained 5 wt. % hydrogen. These estimates are the parenthetical entries in Table 5. By definition gross heat of combustion refers to the amount of energy liberated when a fuel is burned at constant volume with the oxygen and products at the final temperature of 25° C. Water formed in the combustion is in the liquid state. The net heat of combustion refers to the heat evolved when fuel is burned at a constant pressure of 1 atm and 25° C.; all products (including water) are in the gaseous state. See also, ASTM D 4809 "Standard Test Method for Heat of Combustion of Liquid Hydrocarbon Fuels by Bomb calorimeter (Precision method)", ASTM International and SRM 39j; Benzoic Acid calorimetric Standard; National Institute of Standards and Technology, U.S. Department of Commerce: Gaithersburg, Md. (9 Dec. 2004), each hereby incorporated by reference herein.

EXAMPLE 2

A series of trials were conducted to assess the effect of temperature and pressure on the carbon dioxide extraction (21) of corn oil (23) from the corn germ fraction (16) obtained from the corn fractionation process (13).

Trial 1: 100 ml extraction of corn germ: 9200 psi and 90° C. 35.55 g of corn germ feedstock was ground and sieved, and placed in a 100 ml extraction vessel and extracted with pure carbon dioxide at a pressure of 9200 psi and a temperature of 90° C. The flow rate was 4 liters/minute. A total of 8.33 g of yellow corn oil was extracted (23.43% by weight of feedstock). The solvent to feedstock ratio was <8 (S/F<8).

Trial 2: 100 ml extraction of corn germ: 7500 psi and 80° C. 35.55 g of corn germ feedstock was ground and sieved, and placed in a 100 ml extraction vessel and extracted with pure carbon dioxide at a pressure of 7500 psi and a temperature of 80° C. The flow rate was 4 liters/minute. A total of 6.26 g of yellow corn oil was extracted (17.60% by weight of feedstock).

Trial 3: 100 ml extraction of corn germ: 6000 psi and 70° C. 35.55 g of corn germ feedstock was ground and sieved, and placed in a 100 ml extraction vessel and extracted with pure carbon dioxide at a pressure of 6000 psi and a temperature of 70° C. The flow rate was 4 liters/minute. A total of 7.33 g of yellow corn oil was extracted (20.61% by weight of feedstock). Solvent/feed ratio of about 15/1.

Trial 4: 100 ml extraction of corn germ: 5000 psi and 60° C. 35.55 g of corn germ feedstock was ground and sieved, and placed in a 100 ml extraction vessel and extracted with pure carbon dioxide at a pressure of 5000 psi and a temperature of 60° C. The flow rate was 4 liters/minute. A total of 7.38 g of yellow corn oil was extracted (20.75% by weight of feedstock). Solvent/feed ratio of about 25/1.

Trial 5: 100 ml extraction of corn germ: 8000 psi and 85° C. 35.55 g of corn germ feedstock was ground and sieved, and placed in a 100 ml extraction vessel and extracted with pure carbon dioxide at a pressure of 8000 psi and a temperature of 85° C. The flow rate was 4 liters/minute. A total of 7.57 g of yellow corn oil was extracted (21.29% by weight of feedstock). Solvent/feed ratio of about 10/1.

Trial 6: 100 ml extraction of corn germ: 8500 psi and 90° C. 35.55 g of corn germ feedstock was ground and sieved, and placed in a 100 ml extraction vessel and extracted with pure carbon dioxide at a pressure of 8500 psi and a temperature of 90° C. The flow rate was 4 liters/minute. A total of 7.62 g of yellow corn oil was extracted (21.43% by weight of feedstock). Solvent/feed ratio of about 12/1.

Trial 7: 100 ml extraction of corn germ/7500 psi and 90° C. 35.55 g of corn germ feedstock was ground and sieved, and placed in a 100 ml extraction vessel and extracted with pure carbon dioxide at a pressure of 7500 psi and a temperature of 90° C. The flow rate was 4 liters/minute. A total of 7.50 g of yellow corn oil was extracted (21.09% by weight of feedstock). Solvent/feed ratio of about 12/1.

Trail 8: 100 ml extraction of corn germ: 7000 psi and 80° C. 35.55 g of corn germ feedstock was ground and sieved, and placed in a 100 ml extraction vessel and extracted with pure carbon dioxide at a pressure of 7000 psi and a temperature of 80° C. The flow rate was 4 liters/minute. A total of 7.40 g of yellow corn oil was extracted (20.81% by weight of feedstock). Solvent/feed ratio of about 12/1.

Trial 9: 100 ml extraction of corn germ: 6,000 psi and 85° C. 35.55 g of corn germ feedstock was ground and sieved, and placed in a 100 ml extraction vessel and extracted with pure carbon dioxide at a pressure of 6000 psi and a temperature of 85° C. The flow rate was 4 liters/minute. A total of 7.52 g of yellow corn oil was extracted (21.15% by weight of feedstock). Solvent/feed ratio of about 18/1.

Trial 10: 100 ml extraction of corn germ 1600 psi and 20° C. 35.55 g of corn germ feedstock was ground and sieved, and placed in a 100 ml extraction vessel and extracted with pure carbon dioxide at a pressure of 1600 psi and an ambient temperature of 20° C. The flow rate was 4 liters/minute. A total of 4.22 g of yellow corn oil was extracted (11.87% by weight of feedstock). Solvent/feed ratio is >65/1.

As can be easily understood from the foregoing, the basic concepts of the present invention may be embodied in a variety of ways. The invention involves numerous and varied energy production devices and methods of producing energy from products derived from kernel fractionation processes.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "mill" should be understood to encompass disclosure of the act of "milling"—whether explicitly discussed or not—and, conversely, were there effectively disclosure of the act of "milling", such a disclosure should be understood to encompass disclosure of a "mill" and even a "means for milling." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

Thus, the applicant(s) should be understood to claim at least: i) each of the kernel fractionation devices or systems herein disclosed and described, the related methods disclosed and described, similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification are hereby incorporated by reference as part of this description of the invention; and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth below are intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A system for producing ethanol, wherein said system comprises:

fractionating corn to generate a plurality of corn fractions, including a corn bran fraction, a corn germ fraction, and a corn endosperm fraction;

heating said corn endosperm fraction with water to generate mash;

fermenting said mash to generate beer;

distilling said beer to produce ethanol;

extracting an amount of corn oil from said corn germ fraction to produce corn germ cake;

burning said corn germ cake to yield thermal energy; and introducing said thermal energy into the system.

2. The system for producing ethanol as described in claim 1, further comprising burning an amount of said corn bran fraction.

3. The system for producing ethanol as described in claim 1, further comprising the steps of:

producing an amount of biodiesel from said amount of corn oil;

burning said amount of biodiesel to yield thermal energy; and introducing said thermal energy into the system.

4. The system for producing ethanol as described in claim 3, further comprising the step of distilling said amount of beer to generate an ethanol fraction and an amount of still bottoms.

5. The system for producing ethanol as described in claim 4, wherein said ethanol fraction comprises an amount of ethanol and an amount of fusel oil.

6. The system for producing ethanol as described in claim 5, wherein said still bottoms comprise an amount of still bottom liquids and an amount of still bottom solids.

7. The system for producing ethanol as described in claim 6, further comprising the steps of:
   separating said still bottom solids from said still bottom liquids;
   condensing said still bottom liquids;
   burning an amount of condensed still bottom liquids to yield thermal energy; and
   introducing said thermal energy into the system.

8. The system for producing ethanol as described in claim 7, further comprising the steps of:
   separating said amount of ethanol from said amount of fusel oil;
   burning said amount of fusel oil to yield thermal energy; and
   introducing said thermal energy into the system.

9. The system for producing ethanol as described in claim 8, further comprising the steps of:
   burning said amount of ethanol to generate thermal energy; and
   introducing said thermal energy into the system.

10. The system for producing ethanol as described in claim 9, further comprising the steps of:
    burning an amount of natural gas to generate thermal energy; and
    introducing said thermal energy into the system.

11. The system for producing ethanol as described in claim 10, further comprising the steps of:
    burning an amount of coal to generate thermal energy; and
    introducing said thermal energy into the system.

12. The system for producing ethanol as described in claim 11, further comprising the step of adjusting the ratio of said amount of corn bran fraction, said amount of corn germ fraction, said amount of corn germ cake, said amount of corn oil, said amount of biodiesel, said amount of fusel oil, and said amount of condensed still bottom liquids burned to produce thermal energy.

13. The system for producing ethanol as described in claim 12, further comprising the step of adjusting the rate at which said amount of corn bran fraction, said amount of corn germ fraction, said amount of corn germ cake, said amount of corn oil, said amount of biodiesel, said amount of fusel oil, and said amount of condensed still bottom liquids are burned to produce thermal energy.

14. The system for producing ethanol as described in claim 13, further comprising the step of drying said still bottom solids to produce a fractionated corn gluten meal.

15. The system for producing ethanol as described in claim 13, further comprising the step of generating an amount of steam with said amount of thermal energy.

16. The system for producing ethanol as described in claim 15, further comprising the step of operably coupling said amount of steam to a turbine to generate an amount of electricity.

17. The system of claim 1, further comprising determining, prior to extracting an amount of corn oil, an amount of corn oil to be extracted.

18. The system of claim 17, further comprising adjusting the amount of corn oil extracted.

19. The system of claim 1, wherein said extracting an amount of corn oil comprises extracting all or some of the oil contained in the corn germ fraction.

* * * * *